(12) United States Patent
Brandt

(10) Patent No.: US 7,068,752 B2
(45) Date of Patent: Jun. 27, 2006

(54) METHOD AND ARRANGEMENT FOR MEDICAL X-RAY IMAGING

(75) Inventor: Sami Brandt, Espoo (FI)

(73) Assignee: Instrumentarium Corp., Tuusula (FI)

( * ) Notice: Subject to any disclaimer, the term of this patent is extended or adjusted under 35 U.S.C. 154(b) by 57 days.

(21) Appl. No.: 10/813,563

(22) Filed: Mar. 30, 2004

(65) Prior Publication Data

US 2005/0105694 A1    May 19, 2005

(30) Foreign Application Priority Data

Nov. 14, 2003   (FI) ................................. 20031662

(51) Int. Cl.
*A61B 6/00*    (2006.01)

(52) U.S. Cl. .............................. 378/62; 378/4; 378/22; 378/901

(58) Field of Classification Search .................... 378/4, 378/8, 15, 22, 62, 901
See application file for complete search history.

(56) References Cited

U.S. PATENT DOCUMENTS

| | | | |
|---|---|---|---|
| 6,226,409 B1 * | 5/2001 | Cham et al. ................. | 382/228 |
| 6,314,204 B1 * | 11/2001 | Cham et al. ................. | 382/228 |
| 6,353,679 B1 * | 3/2002 | Cham et al. ................. | 382/228 |
| 6,507,633 B1 * | 1/2003 | Elbakri et al. ................. | 378/8 |

FOREIGN PATENT DOCUMENTS

| WO | WO 00/77719 | 12/2000 |
|---|---|---|
| WO | WO 2004/019782 | 3/2004 |

OTHER PUBLICATIONS

Mohammad-Djafari: "Fusion of X ray radiographic data and anatomical data in computed tomography", international Conference on Image Processing; Rochester, NY, Sep. 22-25, 2002.

Mohammad-Djafari: "Fusion of X ray and geometrical data in computed tomography for non-destructive testing applications", International Conference on Information Fusion; Annapolis, MD, Jul. 7-11, 2002.

Odry et al.: "Toward Patient Indentification using Chest CT Scan" WBMA '03; Berkeley, CA, Nov. 8, 2003.

Mohammad-Djafari et al.: "A Scale Invariant Bayesian Method to Solve Linear Inverse Problems", International Workshop on Maximum Entropy and Bayesian Methods; Santa Barbara, CA, 1995.

* cited by examiner

*Primary Examiner*—David V Bruce

(57) ABSTRACT

A medical X-ray device 5 arrangement for producing three-dimensional information of an object 4 in a medical X-ray imaging comprises an X-ray source 2 for X-radiating the object from at least two different directions; a detector 6 for detecting the X-radiation to form projection data of the object 4; a computational device 15 for modelling the object 4 mathematically utilizing the projection data to solve the imaging geometry and/or the motion of the object, where the solving concerns either some or all parts of the imaging geometry and/or the motion of the object. The computational device 15 utilizes said projection data and said mathematical modelling of the object in Bayesian inversion based on Bayes' formula $$p(x, \theta \mid m) = \frac{p_{pr}(\theta) p_{pr}(x) p(m \mid x, \theta)}{p(m)}$$

to produce three-dimensional information of the object.

36 Claims, 9 Drawing Sheets

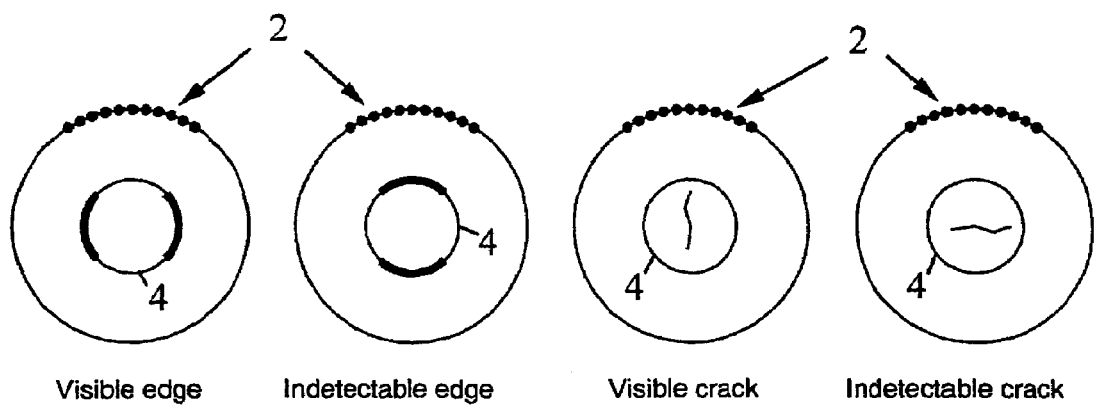
Visible edge   Indetectable edge      Visible crack   Indetectable crack
*Fig.4a*                    *Fig.4B*

Traditional tomosynthesis    Invention

METHOD AND ARRANGEMENT FOR MEDICAL X-RAY IMAGING

CROSS REFERENCE TO RELATED APPLICATION

The present application claims priority from Finnish Patent Application No. 20031662, filed Nov. 14, 2003.

BACKGROUND OF THE INVENTION

Three-dimensional X-ray imaging is based on taking several 1-D or 2-D projection images of a 3-D body from different directions. If 1-D projection images are available from all around a 2-D slice of the body with dense angular sampling, the inner structure of the slice can be determined. This is known as Computerized Tomography (CT) imaging technology, which is widely used in medicine today. A crucial part of CT technology is the reconstruction algorithm taking the X-ray images as argument and producing a voxel representation of the 3-D body.

In many practical cases X-ray projection images are available only from a limited angle of view. A collection of X-ray images of a 3-D body is called sparse projection data if (a) the images are taken from a limited angle of view or (b) there are only a small number of images. Sparse projection data does not contain sufficient information to completely describe the 3-D body.

However, some a priori information about the body is typically available without X-ray imaging. Combining this information with sparse projection data enables more reliable 3-D reconstruction than is possible by using only the projection data.

Traditional reconstruction algorithms such as filtered backprojection (FBP), Fourier reconstruction (FR) or algebraic reconstruction technique (ART) do not give satisfactory reconstructions from sparse projection data. Reasons for this include requirement for dense full-angle sampling of data, difficulty to use a priori information, for example nonnegativity of the X-ray attenuation coefficient, and poor robustness against measurement noise. For example the FBP method relies on summing up noise elements with fine sampling, leading to unnecessarily high radiation dose.

The traditional setting of the image reconstruction problem in tomography assumes that the imaging geometry is known accurately. The prior art requires either reference feature points, with which the unknown part of the imaging geometry (e.g. motion of the imaging device or the object) is computed, or precise prior knowledge of the imaging geometry. Anyway the prior art does not know effective methods to determine the imaging geometry like the motion of the imaging device and/or the object, though all parts of the imaging geometry are rarely precisely known in advance.

BRIEF DESCRIPTION OF THE INVENTION

The aim of the invention is to overcome the problems met in 3-D reconstruction of the object that occur when using traditional reconstruction algorithms with sparse projection data. This is achieved by a method for producing three-dimensional information of an object in medical X-ray imaging. The object is X-radiated from at least two different directions and the said X-radiation is detected to form projection data of the object. The object is modelled mathematically utilizing the projection data to solve the |[s1] imaging geometry|[s2] and/or the motion of the object. Said projection data and said mathematical modelling of the object are utilized in Bayesian inversion based on Bayes' formula $$p(x, \theta | m) = \frac{p_{pr}(\theta) p_{pr}(x) p(m | x, \theta)}{p(m)}$$

to produce three-dimensional information of the object, the prior distribution $p_{pr}(\theta)$ representing the prior knowledge of the imaging geometry| and/or the motion of the object, the prior distribution $p_{pr}(x)$ representing mathematical modelling of the object, x representing the object image vector, which comprises values of the X-ray attenuation coefficient inside the object, $\theta$ representing the parameter vector of the imaging geometry| and/or the motion of the object, m representing projection data, the likelihood distribution $p(m|x,\theta)$ representing the X-radiation attenuation model between the object image vector x, geometry parameter vector $\theta$ and projection data m, p(m) being a normalization constant and the posteriori distribution $p(x,\theta|m)$ representing the three-dimensional information of the object and the imaging geometry including the motion of the object|.

The invention also relates to a medical X-ray device arrangement for producing three-dimensional information of an object (4) in a medical X-ray imaging. The medical X-ray device arrangement comprises:

an X-ray source for X-radiating the object from at least two different directions a detector for detecting the X-radiation to form projection data of the object means for modelling the object mathematically |[s1]utilizing the projection data to solve the imaging geometry and/or the motion of the object, where the solving concerns either some or all parts of the imaging geometry and/or the motion of the object. and the medical X-ray device arrangement includes:

means for utilizing said projection data and said mathematical modelling of the object in Bayesian inversion based on Bayes' formula $$p(x, \theta | m) = \frac{p_{pr}(\theta) p_{pr}(x) p(m | x, \theta)}{p(m)}$$

to produce three-dimensional information of the object, the prior distribution ppr($\theta$) representing the prior knowledge of imaging geometry and/or the motion of the object (4), the prior distribution ppr(x) representing mathematical modelling of the object, x representing the object image vector, which comprises values of the X-ray attenuation coefficient inside the object, $\theta$ representing the parameter vector of the imaging geometry and/or the motion of the object (4), m representing projection data, the likelihood distribution $p(m|x,\theta)$ representing the X-radiation attenuation model between the object image vector x. geometry parameter vector $\theta$ and projection data m, p(m) being a normalization constant and the posteriori distribution $p(x,\theta|m)$ representing the three-dimensional information of the object (4) and the imaging geometry including the motion of the object.

In this invention, the imaging geometry and/or the motion of the object are solved with the image reconstruction simultaneously or having different timings. This is based on that projection data itself simultaneously contains sufficient amount of information about the imaging geometry and the 3D reconstruction. Neither reference feature points nor prior knowledge of the motion are needed.

The invention is also based on that biological issues have that kind of statistical a priori information that this information can be success fully utilized with Bayesian inversion in medical x-ray imaging. The suitable a priori information makes possible to model the biological tissue mathematically accurately enough and independently of X-ray imaging. From biological tissue it is possible to compile qualitative structural information which makes it possible to utilize the Bayesian method successfully to solve the problems in medical three-dimensional x-ray imaging. There is certain regularity in biological tissues and this regularity is useful especially with the Bayesian method.

For example 10 X-ray images are taken from breasts of different persons. From these x-ray images it is noticed that there is much similarity in the statistical structure of the breasts between different people. In other words biological tissues and x-ray images taken from the biological tissues have similar or almost similar statistical structure between different persons.

With Bayesian inversion it is possible to utilize a priori information efficiently in 3-D reconstruction from sparse projection data, because the suitable a priori information from the biological tissue makes possible to model the biological tissue mathematically accurately enough and independently of X-ray imaging. In addition, a priori information of the imaging geometry, such as approximate positions of the radiation source and the detector, can be similarly taken into account in a sound, statistical way. Any collection of projection data can be used in the reconstruction. Application-dependent a priori knowledge can be used to regularize the ill-posed reconstruction problem.

This invention improves the quality of 3-D reconstructions over traditional methods. In addition, the number of radiographs can be minimized without compromising quality of the reconstruction. This is very important in medical applications since the X-ray dose of the patient can be lowered.

BRIEF DESCRIPTION OF THE FIGURES

FIGS. 4A–4B show examples of parts of boundaries and cracks of an object visible and invisible without a priori information.

DETAILED DESCRIPTION OF THE INVENTION

Figure 1:
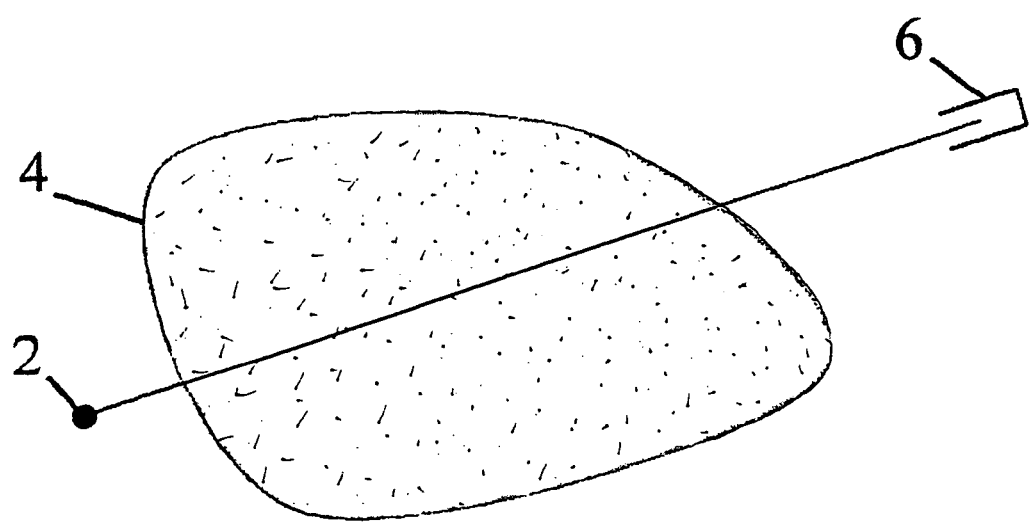
FIG. 1 shows a simple example of X-ray imaging.

In conventional tomography, the interior of an object is reconstructed from tomographic projections such as X-ray images. All the current image reconstruction methods assume that projection geometry of the imaging device is either known or solved in advance by using fiducial or non-fiducial feature points in the images. With this invention a novel approach is presented where the imaging geometry is solved with the reconstruction problem while no correspondence information is needed. This approach is a direct application of Bayesian inversion theory and produces the maximum likelihood or maximum a posteriori estimates for the imaging geometry like motion parameters under the selected noise and prior distributions. This invention can be utilized assuming either 1D or 2D projections. To utilize the invention with 1D projections is also often a sufficient assumption since the reconstruction problem is frequently performed as a stack of 2D reconstruction problems for computational reasons. However, the method can be also directly extended to the general 3D case.

In practical imaging situations X-ray images are not always available from all around the body. The body might be visible only from certain directions due to imaging geometry. For example this is the case in 3-D mammography with the breast compressed against the detector, or in intraoral dental imaging with the detector inside the patient's mouth. This situation is called limited-angle tomography. Also, the region of interest might be surrounded by tissue that need not be imaged, like in extraoral dental imaging. This situation is called local tomography. In addition the number of radiographs should be minimized in medical applications for reducing the X-ray dose of the patient.

In the preferred embodiments of the invention Bayesian inversion algorithms are used to create a new type of 3-D medical X-ray imaging. It is intermediate between a projection radiograph and a full computed tomography scan. Two steps are needed to perform successfully such imaging: In step one, the doctor (a) collects all the prior information he or she has on the tissue of interest, and (b) takes the minimum number of radiographs containing the desired 3D information. In step two, a tomographic algorithm based on Bayesian inversion is used for 3D reconstruction. The algorithm contains two separate mathematical models. First, all a priori information (i.e. information that is independent of X-ray imaging) is used to model the unknown object mathematically. The model is put into the form of prior distribution in Bayes' formula. In addition, prior information of the imaging geometry parameters can be modelled. Second, the measurement is modelled mathematically. This involves the geometry of the imaging device, position of the detector and X-ray source during the exposure of each projection image and a model for X-ray attenuation inside tissue. The mathematical model of the measurement is put into the form of likelihood distribution in Bayes' formula.

In FIG. 1 is shown a simple example of X-ray imaging, where an X-ray source 2 is placed on one side of an object 4 under imaging. Radiation passes through the object and is detected by a detector 6 on the other side. The X-ray source is for example a X-ray source of an intraoral X-ray source of a dentist, of a dental panoramic X-ray device, of a surgical C-arm X-ray device, of a mammography device or of any other medical X-ray device and the detector 6 is a detector of some of those devices. Usually the detector 6 is a digital sensor that can be thought of as a 2-D array of almost pointlike detectors.

The 3-D body under imaging is modelled by nonnegative X-ray attenuation coefficient. The value gives the relative intensity loss of the X-ray travelling within a small distance dr:

$$\frac{dI}{I} = -x(r)dr \qquad (1)$$

The X-radiation has initial intensity $I_0$ when entering the object 4 and a smaller intensity $I_0$ when exiting the object. The following equation shows the attenuation law:

$$\int_L x(r)dr = -\int_L \frac{I'(r)}{I(r)}dr = \log I_0 - I_1 \qquad (2)$$

where initial intensity $I_0$ is known by calibration, and intensity after object $I_1$, is known from the corresponding point value in a projection image. Thus the measured data is the integral of x along the line L.

In the above model it is not taken into account (a) scattering phenomena resulting in X-rays changing their direction, or (b) the dependency of attenuation on the X-ray spectrum resulting in low-energy photons being more easily attenuated than high-energy ones. Effect (b) causes errors in measurements and is sometimes referred to as beam hardening. More detailed models can be utilized in Bayesian inversion to overcome (a) and (b).

Figure 2A:
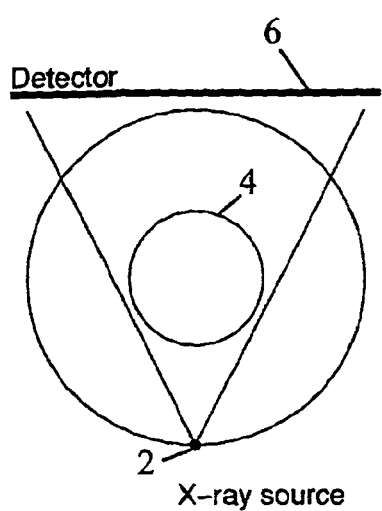
FIGS. 2A–2B show a difference between global tomography and local tomography.
Figure 2B:
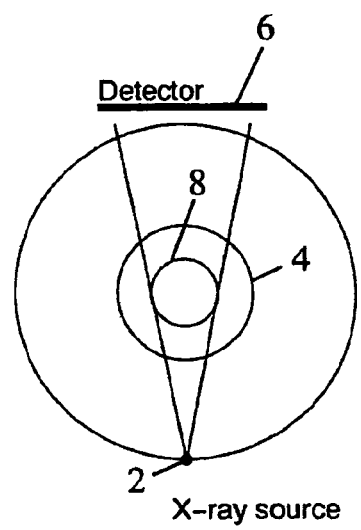

In medical imaging the geometrical arrangements of the X-ray source and digital sensor vary according to the diagnostic task and equipment. FIGS. 2A–2B and 3 illustrate the types of tomographic data resulting from different imaging situations. For clarity, here are presented two-dimensional examples; similar situations can be considered in 3-D.

In FIG. 2A–2B are shown two cases according to whether the whole object 4 is fully visible in each projection or not. These cases are called global tomography and local tomography, respectively. In FIG. 2B is radiated only ROI (Region Of Interest) 8.

Figures 3A, 3B:
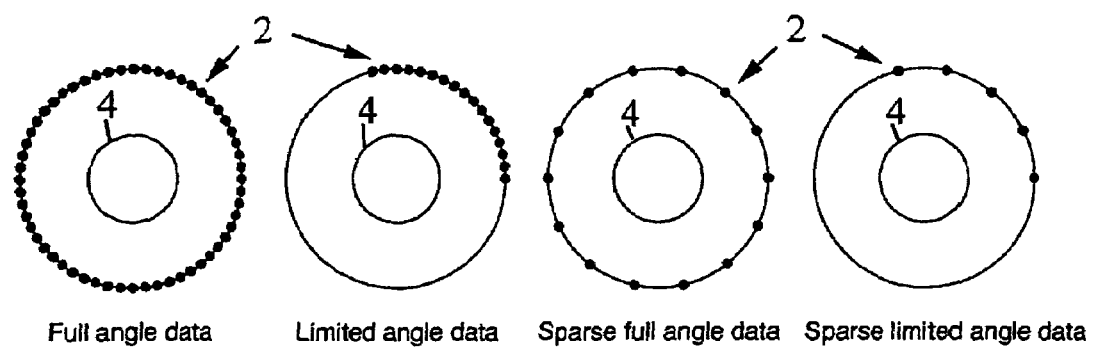
FIGS. 3A–3B show different types of sparse projection data. Every black dot represents a location of the X-ray source for taking one projection image.

The types of data described in FIGS. 3A–3B cover a large range of specific imaging tasks. The choice of data collection dictates what kind of features and details it is easiest to reconstruct reliably from the data. Thus the choice of projection views must be made according to the diagnostic task at hand. In traditional CT imaging, projections are taken from all around the object 4. In the preferred embodiments of the invention radiation dose is lowered by sampling the angular variable more sparsely. FIG. 3A presents more dense angular data with full angle and limited angle measurements. FIG. 3B presents more sparse angular data, also with full and limited angles of measurement.

In FIGS. 4A and 4B there are presented examples of parts of boundary and cracks that are visible or undetectable in reconstruction without a priori information. FIG. 4A there is an object 4 under imaging with edge on the surface of the object. The edge is detectable on the leftmost position where the edge is more parallel to the direction of the X-rays. In the FIG. 4B there is a crack inside of the object 4. The crack is detectable in the leftmost position parallel to the angle of measurement.

The main idea in Bayesian inversion method is to consider the inverse problem as a problem of statistical inference. All variables are redefined to be random variables. The randomness reflects uncertainty of their actual values and the degree of uncertainty is coded in the probability distributions of these random variables.

Figure 5:
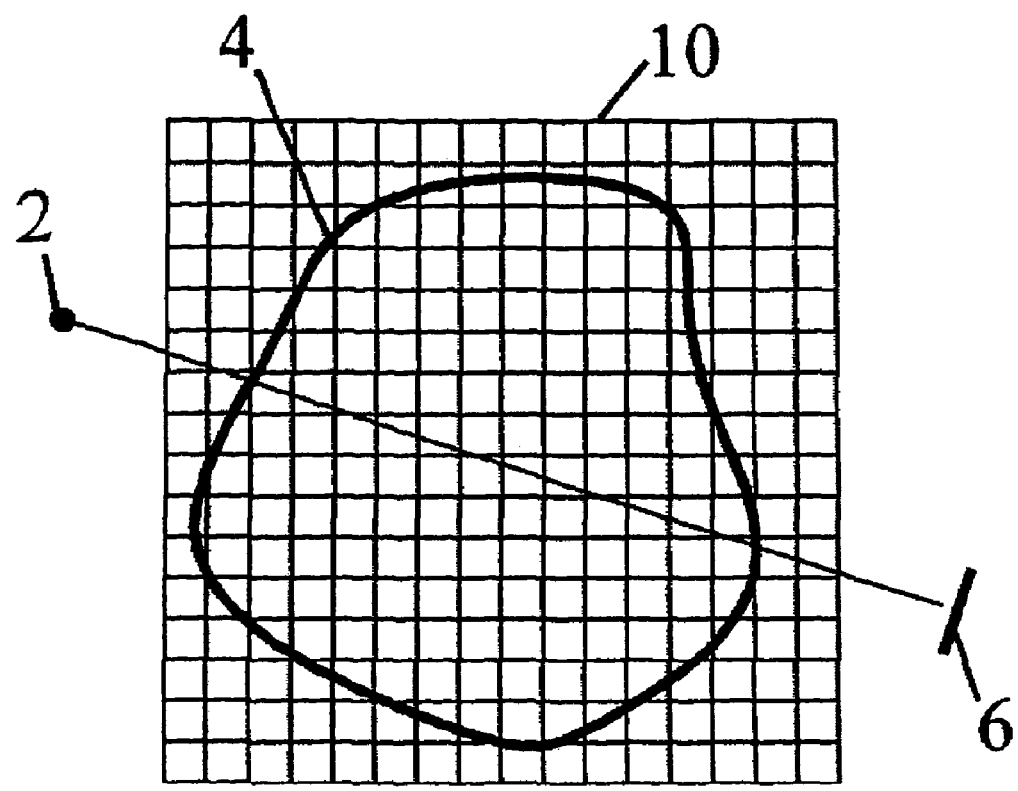
FIG. 5 illustrates "pencil beam" X-ray attenuation model.

Typically, the model for X-ray tomography problem is represented by the formula $$m = Ax + e \qquad (3)$$

where m is a vector of projection measurements (all the projection images represented as one vector), x is a vector that represents the object densities (voxel values) at given positions in 3D space, A is a transformation matrix that characterises how the projections are constructed from the 3D object, hence contains the imaging geometry, and e is a random, noise vector. The variables m, x and e are random variables and the matrix A comes from the pencil beam model for the X-ray attenuation: A contains the weights describing how much each voxel contributes to the X-ray attenuation along the X-ray paths. In this way the integral in formula (2) is approximated. This is illustrated by an example in FIG. 5.

In the traditional setting, the objective is to reconstruct the structure (density) of the object given the projection images and the imaging geometry. As an extension to the traditional setting, in this invention both the reconstruction and the imaging geometry are solved simultaneously. To emphasise that, we write the model (3) in the form $$m = A_\theta x + e,$$

where we just explicitly say that A depends on the geometry parameters θ that define the unknown part of the imaging geometry and motion of the object. Hence, the unknowns in the equation are both θ and x.

Simultaneous solving of both θ and x is possible, because, the model (3) constrains the imaging geometry sufficiently. This is due that, even though there are more unknowns than equations, the equations are not independent and, if e.g. the motion parameters are incorrect, the equations are also inconsistent. Moreover, if the geometry parameters θ were incorrectly fixed, in general, there is no reconstruction x that would produce the observed images m. Therefore, excluding certain special cases, the geometry parameters are completely determined from the noise model, though the image object x is not uniquely (additional prior information is required), as far as the imaged object is sufficiently complex. Therefore any feasible reconstruction x (in the likelihood sense) can be used to compute θ, after which the reconstruction x can be updated to accord best with the prior information.

Assume now that the object image vector x, geometry parameter vector θ, and the noise are jointly independent random variables. The conditional probability distribution of x given the measurement m is given by Bayes' formula in the form $$p(x, \theta | m) = \frac{p_{pr}(\theta) p_{pr}(x) p(m | x, \theta)}{p(m)} \qquad (4)$$

where p(m) is a normalization constant. The density p(x, θ|m) is called the posteriori distribution of x and θ. p(m|x,θ) is a likelihood distribution representing the X-radiation attenuation model between the object image vector x, geometry parameter vector θ, and projection data m.

The density $P_{pr}(x)$, called the prior distribution of x, is designed to contain all possible information available of the actual object 4 independently of X-ray imaging. The density $P_{pr}(\theta)$ is the prior distribution of θ, and it models the available information of the imaging geometry including the motion of the object. If we do not have any such prior information of the parameters θ, we may use the non-informative prior $P_{pr}(θ)$=constant. It is crucial, in contrast to several classical regularization methods, that the choice of the prior distributions should not be based on the projection data. The rule of thumb in the design of prior distributions is that typical image vectors (say, of some existing library) should have high prior probability while atypical or impossible ones should have low or negligible probability.

In the framework of the Bayesian inversion theory, the posterior distribution in formula (4) represents the complete solution of the 3D reconstruction problem as well as of the imaging geometry estimation problem.

To produce an image of the object 4, and similarly an estimate for the geometry parameters, based on the posterior distribution, several alternatives exist. The most common ones are the maximum a posteriori estimator (MAP) and conditional mean estimator (CM). Let y=(x,θ) i.e. y is the vector composed of both the object image and geometry parameter vectors. The estimators are defined by the formulas $$p(y_{MAP}|m) = \max p(y|m) \qquad (5)$$

where the maximum on the right hand side is taken over all y, and $$y_{CM} = \int y p(y|m) dy \qquad (6)$$

Finding the MAP estimator is an optimization problem while finding the CM estimator is a problem of integration.

Figure 6:
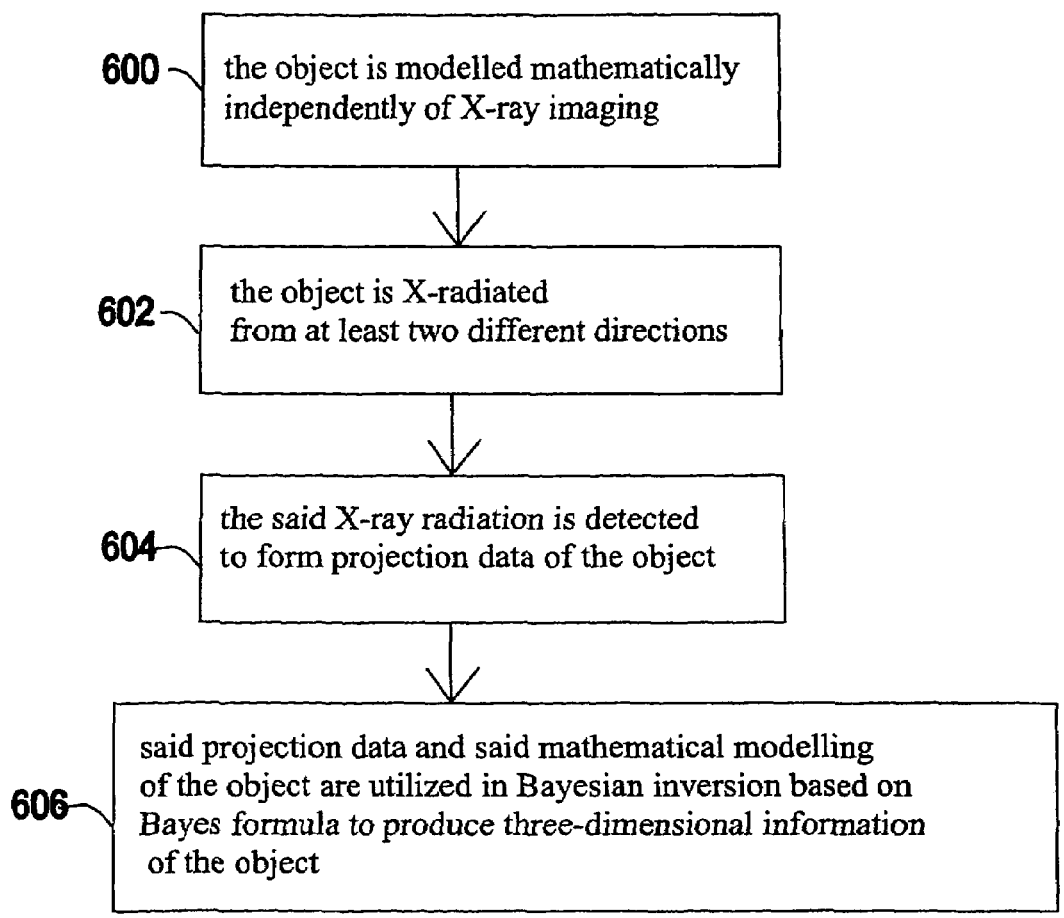
FIG. 6 is basic flow chart of the method according to the invention.

In FIG. 6 is presented a basic flow chart of the method according to the invention. In method step 600 the object is modelled mathematically independently of X-ray imaging. In method step 602 the object is X-radiated from at least two different directions. In method step 604 the said X-radiation is detected to form projection data of the object. In method step 606 said projection data and said mathematical modelling of the object are utilized in Bayesian inversion based on Bayes formula to produce three-dimensional information of the object. The method step 600 is also possible to perform after method step 602 or 604.

In the first preferred embodiment of the invention is presented an application to dental radiology.

X-ray projection images are conventionally used in dental radiology. However, certain diagnostic tasks require more precise knowledge of the 3D structure of tissue than is available in two-dimensional radiographs. Such tasks include implant planning and detection of bone loss between tooth roots.

Figure 7:
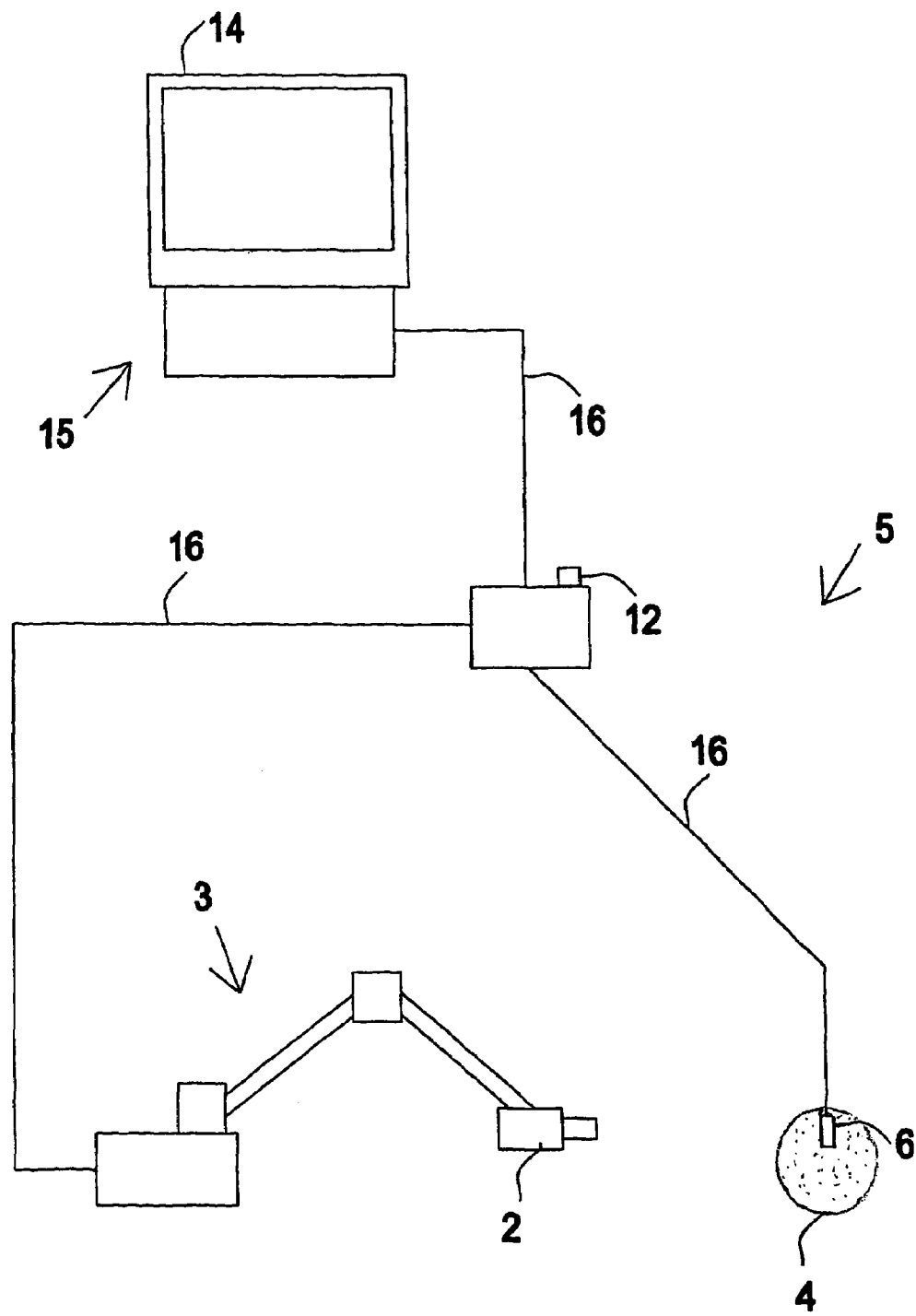
FIG. 7 is an intraoral X-ray device arrangement presenting one preferred embodiment of the invention.

In FIG. 7 is presented an intraoral X-ray device 5 arrangement presenting the first preferred embodiment of the invention. It is important to note that this is only an example of the medical X-ray device 5 arrangement where the invention is possible to be utilized.

The medical x-ray device 5 in the preferred embodiments of the invention is for example a dental panoramic X-ray device, a surgical C-arm X-ray device or a mammography device.

In the first preferred embodiment of the invention the articulated arm arrangement 3 moves the X-ray source 2 to the right position. The X-radiation begins by pressing the exposure button 12. The X-ray source 2 X-radiates the object 4, which is for example teeth of a patient. The detector 6 detects the X-radiation. The image information which is got by detecting the X-radiation is sent by communication link 16 to the computer 14. The computer comprises the software means 15 to process the image information according to the invention. There can be more than one computer 14 and also the software means 15 can situate in more than one computer 14. For example a first computer 14 is a computer which is used in x-ray imaging. A second computer 14 is a computer which is used in processing the image information according to the invention. It is possible to have the second computer 14 far away from the actual medical x-ray device 5. For simplicity in FIG. 7 is shown only one computer 14.

In the first preferred embodiment (FIG. 7) of the invention, the dentist's X-ray equipment is used for taking a set of 2D projection images that are used as input for Bayesian 3D reconstruction algorithm. Such equipment includes an intraoral X-ray unit and a digital intraoral sensor.

Benefits of this approach over conventional CT scan are
   low cost and convenient usage,
   high resolution of the projection images,
   possibility to take as few radiographs as is needed to capture the relevant 3D information, minimizing radiation dose to the patient,
   the possibility to choose imaging directions so that the X-rays do not pass through the whole head but only the interesting tissue, further reducing dose.

In the preferred embodiments of the invention, Bayesian inversion is used for the 3D reconstruction. Input data for the algorithm is the set of projection images and the following a priori knowledge:

(a) Dental tissue consists of few approximately homogeneous regions with well-defined boundaries.

(b) Dental tissue can only attenuate X-radiation, not intensify it.

The example of the detector 6 used in the first preferred embodiment of the invention is based on charge coupled device (CCD) technology and has dynamic range of 4096 gray levels. The size of the active imaging area is 34 mm*26 mm and the resolution is 872*664 pixels. After exposure, each pixel contains an integer which is proportional to the number of X-ray quanta that hit the pixel's area.

Alternative detectors include any other digital intraoral sensor, digitized X-ray film, or any intraoral sensing device converting detected X-ray photons to a digital image.

Figure 8:
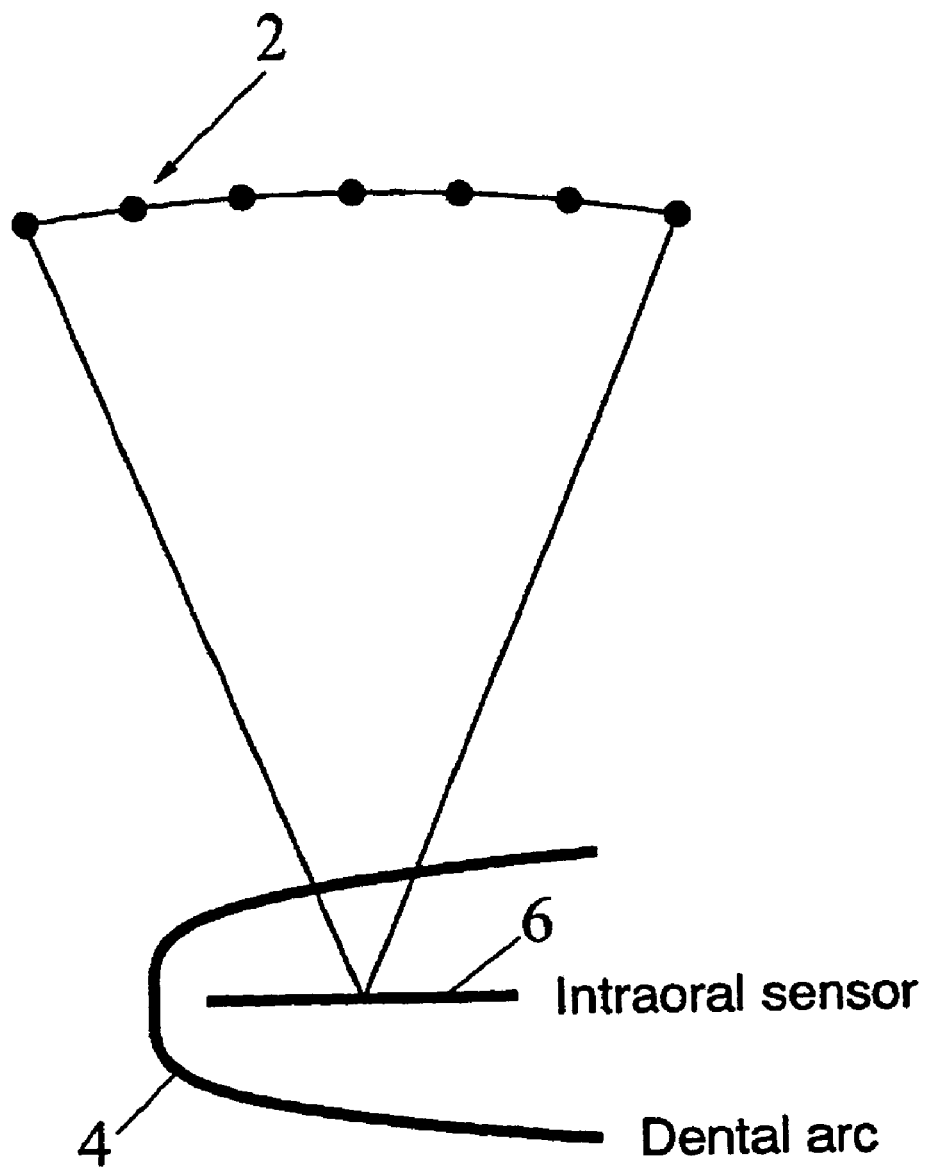
FIG. 8 shows a measurement geometry of dental limited-angle tomography with a digital intraoral sensor.

In the measurement geometry the focal point of the X-ray source 2 moves horizontally on a circle in the plane of the paper, with center at the detector 6, see FIG. 8. In FIG. 8, the detector 6 corresponds to one row of CCD pixels in the CCD sensor.

In FIG. 8 is presented an example of taking seven radiographs of some teeth of a patient. The total opening angle of the projection views is 55 degrees in this example. FIG. 8 represents the xy plane, and the z-coordinate axis is thought to be perpendicular to the plane of the paper.

In the preferred embodiments, mathematical modelling of the object 4 can be done with a prior distribution of the form in formula (7):

$$p_{pr}(x) = \exp\left(-\alpha \sum_N U_N(x)\right) \qquad (7)$$

where the sum is taken over a collection of 3D neighbourhoods N and the value $U_N(x)$ depends only on the values of voxels belonging to the neighborhood N, and α is a positive regularization parameter used to tune the width of the prior distribution. The neighborhood N is typically a set of voxels whose center points are closer to each other than some predefined maximum distance.

It is to be noted that formula (7) does not define a probability distribution since it does not integrate to 1. Instead, the integral diverges. However, when used in the Bayes formula (4) with a suitable likelihood distribution, the posterior distribution is integrable. The same remark concerns the priors derived from (7), that is, formulae (9), (10) and (11).

In the preferred embodiments of the invention the three-dimensional problem can be reduced to a stack of two-dimensional problems each corresponding to a plane determined by a constant value of z. Here FIG. 8 represents exactly the situation in the xy plane, i.e. the plane z=0. Each row in the detector corresponds to one such 2D problem. This approach leads to small approximation error because the X-ray source does not move in the correct plane for nonzero z, and this error is neglected.

Next the modeling of a 2D tomographic problem is explained. Let $$m(j) = A\, x(j) + e(j) \quad (8)$$

denote the jth 2D tomographic problem. Here the vector m(j) contains the readings on jth row from each of the seven radiographs. The vector x(j) is the jth slice of the 3-D representation x of the object 4 under imaging. The matrix A is the pencil beam model matrix for the 2-D tomography problem. Now x(j) is a 2D array of pixels. The pixels are denoted by x(j)[k,q], where k=1, 2, ..., K is row index and q=1, 2, ..., Q is column index.

The mathematical modelling of the object 4, i.e. incorporation of prior information, is next explained for the 2D slice. Define $$P_{pr}(x^{(j)}) = \exp\left(-\alpha \sum_{k=1}^{K} \sum_{q=1}^{Q} U(N(x^{(j)}[k,q]))\right) \quad (9)$$

where the value U(N(x(j)[k,q])) depends only on the values of pixels belonging to the neighborhood N of the pixel x(j)[k,q] and α is a positive regularization parameter used to tune the width of the prior distribution. The choice of the neighborhoods N(x(j)[k,q]) is arbitrary, but a typical choice is the set of pixels whose centerpoints are closer to the centerpoint of x(j)[k,q] than some predefined distance.

In the preferred embodiment, the neighborhoods are chosen to consist of two adjacent pixels. Further, the function U is chosen to be a power of absolute value of the difference between adjacent pixels. These choices lead to formula (10):

$$P_{pr}(x^{(j)}) = \exp\left(-\alpha\left(\sum_{k=1}^{K-1}\sum_{q=1}^{Q}|x^{(j)}[k,q]-x^{(j)}[k+1,q]|^s ++ \right.\right.$$
$$\left.\left.\sum_{k=1}^{K}\sum_{q=1}^{Q-1}|x^{(j)}[k,q]-x^{(j)}[k,q+1]|^s\right)\right) \quad (10)$$

where s is a positive real number and α is a regularization parameter used to tune the width of the prior distribution.

In the equation (11) is presented non-normalized total variation (TV) distribution, when s=1 in equation (10). This is the case according to the preferred embodiment of the invention, because when s=1 the prior model becomes such that it gives high probability for objects consisting of a few areas of different attenuation with well-defined boundaries.

$$prTV(x^{(j)}) = \exp\left(-\alpha\left(\sum_{k=1}^{K-1}\sum_{q=1}^{Q}|x^{(j)}[k,q]-x^{(j)}[k+1,q]| ++ \right.\right.$$
$$\left.\left.\sum_{k=1}^{K}\sum_{q=1}^{Q-1}|x^{(j)}[k,q]-x^{(j)}[k,q+1]|\right)\right) \quad (11)$$

X-radiation can only attenuate, not strengthen, inside tissue. This leads to positivity prior pos defined by $$pos(x(j))=1 \text{ if all pixels of } x(j) \text{ are positive, 0 otherwise} \quad (12)$$

The explanation of modeling of one 2D tomographic problem is now complete.

The stack of 2D problems are connected to each other by demanding that consecutive 2D slices x(j) and x(j−1) should not be very different.

Mathematically this is expressed as follows:

$$pr3D(x(j)) = \exp(-\gamma \Sigma\Sigma |x(j)[k,q] - x(j-1)[k,q]|), \quad (13)$$

where the sums are taken over k=1, ..., K and q=1, ..., Q and γ>0 is another regularization parameter. So the prior distribution in formula (4) is the product of (11), (12) and (13):

$$P_{pr}(x(j)) = prTV(x(j))pos(x(j))pr3D(x(j)). \quad (13)$$

The measurements are taken into account in the form of the likelihood distribution $$P(m^{(j)} | w^{(j)}) = c\exp\left\{-\frac{1}{2}(m^{(j)} - Ax^{(j)})^T \Sigma^{-1} (m^{(j)} - Ax^{(j)})\right\} \quad (15)$$

where Σ is the covariance matrix of the Gaussian noise vector e. c is a normalization constant.

In reality, X-radiation measurement noise is Poisson distributed. Formula 15 uses a Gaussian approximation to the Poisson distribution.

All the parts are presented of the right hand side of (4). Next it is looked for the MAP estimate of x(j), that is, the image x(j) that gives the largest value for the posteriori distribution (4). This is equivalent to finding the image x(j) that minimizes the expression $$F(x^{(j)}) = \frac{1}{2}(m^{(j)} - Ax^{(j)})^T \Sigma^{-1}(m^{(j)} - AX^{(j)}) + $$
$$-\log(prTV(x^{(j)})) - \log(pr3D(x^{(j)})) \quad (16)$$

with the additional requirement that every pixel of x(j) is positive.

Minimization of (16) is difficult since F is not a differentiable function due to the absolute values present in (11)

and (13) and due to the sharp cutting in (12). The absolute values in (11) and (13) are replaced by $$|t| \approx h_\beta(t) = \frac{1}{\beta}\log(\cosh(\beta t)) \quad (17)$$

where $\beta>0$, enabling the use of efficient gradient-based minimization routines. The positivity constraint is taken care of by an interior search minimization method.

Figure 9:
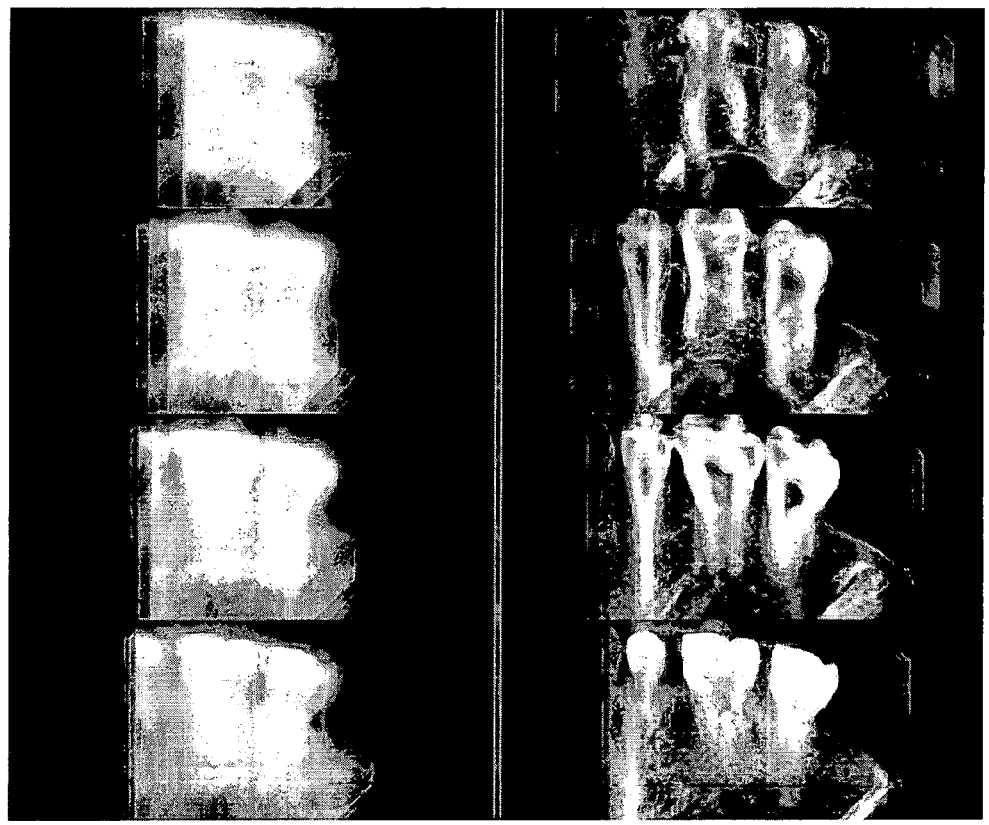
FIG. 9 shows results of 3D reconstruction of head phantom in the first preferred embodiment.

The results are shown in FIG. 9 in comparison with traditional tomosynthesis technique based on backprojection.

In this description explained mathematic modelling and other image information processing are performed by software means 15 to accomplish three-dimensional information of the object 4.

In the second preferred embodiment the invention is utilized in dental panoramic x-ray imaging. The object 4 is typically teeth of the patient and the medical x-ray device 5 arrangement is dental panoramic x-ray device arrangement.

In the third preferred embodiment the invention is utilized in mammography, for example in FFDM (Full Field Digital Mammography). There the object 4 is breast of human being and the medical x-ray device 5 arrangement is mammography device arrangement.

In the fourth preferred embodiment the invention is utilized in surgical x-ray imaging. There the object 4 is the body part under surgery and the medical x-ray device 5 arrangement is surgical x-ray device arrangement.

In the first, second, third and fourth preferred embodiments of the invention the basic method steps are the same as mentioned with the flow chart in FIG. 6. The utilizing of the invention in the second, third and fourth preferred embodiment is similar to what is described with the first preferred embodiment of the invention and elsewhere in this application except for different medical x-ray imaging applications and their differences because of different medical x-ray devices and different objects to be x-ray imaged.

What makes this invention especially inventive is that the imaging geometry and/or the motion of the object is solved with the image reconstruction simultaneously or having different timings. This is based on that projection data itself contains sufficient information about the imaging geometry and also sufficient information about the 3D reconstruction. Neither reference feature points nor prior knowledge of the motion are needed.

This can be done as described above with the preferred embodiments and with the means 15 for modelling the object 4 mathematically utilizing the projection data to solve the imaging geometry and/or the motion of the object and with the means 15 for utilizing said projection data and said mathematical modelling of the object in Bayesian inversion based on Bayes' formula $$p(x,\theta|m) = \frac{p_{pr}(\theta)p_{pr}(x)p(m|x,\theta)}{p(m)}$$

to produce three-dimensional information of the object, the prior distribution $p_{pr}(\theta)$ representing the prior knowledge of the imaging geometry and/or the motion of the object 4, the prior distribution $p_{pr}(x)$ representing mathematical modelling of the object, x representing the object image vector, which comprises values of the X-ray attenuation coefficient inside the object, $\theta$ representing the parameter vector of the imaging geometry and/or the motion of the object, m representing projection data, the likelihood distribution p(m|x, $\theta$) representing the X-radiation attenuation model between the object image vector x and projection data m, geometry parameter vector $\theta$, p(m) being a normalization constant and the posteriori distribution p(x,$\theta$|m) representing the three-dimensional information of the object 4 and the imaging geometry including the motion of the object.

Although the invention is described above with reference to the examples illustrated in the attached figures, it is to be understood that the invention is not limited thereto but can be varied in many ways within the inventive idea disclosed in the attached claims.

The invention claimed is:

1. A method for producing three-dimensional information of an object (4) in medical X-ray imaging, characterized in that the object is X-radiated from at least two different directions and the said X-radiation is detected to form projection data of the object (4)

the object is modelled mathematically utilizing the projection data to solve the imaging geometry and/or the motion of the object, where the solving concerns either some or all parts of the imaging geometry and/or the motion of the object and said projection data and said mathematical modelling of the object are utilized in Bayesian inversion based on Bayes' formula $$p(x,\theta|m) = \frac{p_{pr}(\theta)p_{pr}(x)p(m|x,\theta)}{p(m)}$$

to produce three-dimensional information of the object, the prior distribution ppr($\theta$) representing the prior knowledge of the imaging geometry and/or the motion of the object (4), the prior distribution ppr(x) representing mathematical modelling of the object, x representing the object image vector, which comprises values of the X-ray attenuation coefficient inside the object, $\theta$ representing the parameter vector of the imaging geometry and/or the motion of the object (4), m representing projection data, the likelihood distribution p(m|x,$\theta$) representing the X-radiation attenuation model between the object image vector x, geometry parameter vector $\theta$, and projection data m, p(m) being a normalization constant and the posteriori distribution p(x,$\theta$|m) representing the three-dimensional information of the object (4) and the imaging geometry including the motion of the object.

2. A method according to claim 1, characterized in that the three-dimensional information of the object (4) is one or more two-dimensional images representing X-ray attenuation coefficient along slices through the object.

3. A method according to claim 1, characterized in that the three-dimensional information of the object (4) is a three-dimensional voxel representation of the X-ray attenuation in the object.

4. A method according to claim 1, characterized in that the measurement model is m=A$\theta$x+e, where matrix A$\theta$ contains the weights describing how much each voxel contributes to the X-ray attenuation along the X-ray paths and the noise e is independent of object image vector x and the geometry parameter vector θ leading to the likelihood distribution $$p(m|x,\theta)=p_{noise}(m-A_\theta x).$$

5. A method according to claim 1, characterized in that the said mathematical modelling comprises that X-radiation attenuates when passing the object (4), which means that every image voxel is nonnegative.

6. A method according to claim 1, characterized in that mathematical modelling is expressed by the formula:

$$p_{pr}(x) = \exp\left(-\alpha\sum_N U_N(x)\right)$$

where the sum is taken over a collection of 3D neighbourhoods N and the value $U_N(x)$ depends only on the values of voxels belonging to the neighborhood N, and a is a positive regularization parameter used to tune the width of the prior distribution.

7. A method according to claim 1, characterized in that the 3D tomographic problem is divided into a stack of 2D tomographic problems and on every such 2D problem, the mathematical modelling is expressed by the formula:

$$p_{pr}(x) = \exp\left(-\alpha\sum_N U_N(x)\right)$$

where the sum is taken over a collection of 2D neighbourhoods N and the value $U_N(x)$ depends only on the values of pixels belonging to the neighborhood N, and α is a positive regularization parameter used to tune the width of the prior distribution, and the 2D tomographic problems are related to each other by the formula $$pr3D(x(j))=\exp(-\gamma\Sigma\Sigma|x(j)[k,q]-x(j-1)[k,q]|),$$

where the sums are taken over all pixels (k=1, . . . , K, q=1, . . . , Q) and y>0 is another regularization parameter.

8. A method according to claim 7, characterized in that the neighborhoods comprise two adjacent pixels and U calculates a power of the absolute value of the difference, leading to the formula $$P_{pr}(x^{(j)}) = \exp\left(-\alpha\left(\sum_{k=1}^{K-1}\sum_{q=1}^{Q}|x^{(j)}[k,q]-x^{(j)}[k+1,q]|^s + \sum_{k=1}^{K}\sum_{q=1}^{Q-1}|x^{(j)}[k,q]-x^{(j)}[k,q+1]|^s\right)\right)$$

where s is a positive real number.

9. A method according to claim 8, characterized in that s=1 corresponding to total variation (TV) prior describing objects (4) consisting of different regions with well-defined boundaries.

10. A method according to claim 1, characterized in that mathematical modelling is qualitative structural information of the target where the structural information is encoded in prior distributions that are concentrated around object image vectors x that correspond to the physiological structures of the object (4).

11. A method according to claim 1, characterized in that mathematical modelling comprise a list or probability distribution of possible attenuation coefficient values in the object (4).

12. A method according to claim 1, characterized in that the X-ray imaging geometry, such as X-ray source position, has unknown error modelled in the distribution p(m|x,θ).

13. A method according to claim 1, characterized in that the X-radiation measurement noise is Poisson distributed.

14. A method according to claim 1, characterized in that the medical X-ray imaging is dental radiography.

15. A method according to claim 1, characterized in that the medical X-ray imaging is surgical C-arm imaging.

16. A method according to claim 1, characterized in that the medical X-ray imaging is mammography.

17. A method according to claim 1, characterized in that three-dimensional information of the object (4) is produced on the basis of the maximum a posteriori estimator (MAP) which is calculated by the equation:

$$p(y_{MAP}|m)=\max p(y|m)$$

m representing projection data and y=(x,θ) representing the vector composed of the object image vector and the geometry parameter vector and where the maximum on the right hand side of the equation is taken over all y.

18. A method according to claim 1, characterized in that three-dimensional information of the object (4) is produced on the basis of the conditional mean estimator (CM), which is calculated by the equation:

$$y_{CM}=\int yp(y|m)dy$$

where m represents projection data and y=(x,θ) represents the vector composed of the object image vector and the geometry parameter vector.

19. A medical X-ray device (5) arrangement for producing three-dimensional information of an object (4) in a medical X-ray imaging, characterized in that the medical X-ray device (5) arrangement comprises:

an X-ray source (2) for X-radiating the object from at least two different directions a detector (6) for detecting the X-radiation to form projection data of the object (4)

means (15) for modelling the object (4) mathematically utilizing the projection data to solve the imaging geometry and/or the motion of the object, where the solving concerns either some or all parts of the imaging geometry and/or the motion of the object and the medical X-ray device (5) arrangement includes means (15) for utilizing said projection data and said mathematical modelling of the object in Bayesian inversion based on Bayes' formula $$p(x,\theta|m) = \frac{p_{pr}(\theta)p_{pr}(x)p(m|x,\theta)}{p(m)}$$

to produce three-dimensional information of the object, the prior distribution $p_{pr}(\theta)$ representing the prior knowledge of the imaging geometry and/or the motion of the object (4), the prior distribution $p_{pr}(x)$ representing mathematical modelling of the object, x representing the object image vector, which comprises values of the X-ray attenuation coefficient inside the object, θ representing the parameter vector of the imaging geometry and/or the motion of the object (4), m representing projection data, the likelihood distribution p(m|x,θ)

representing the X-radiation attenuation model between the object image vector x, geometry parameter vector θ, and projection data m, p(m) being a normalization constant and the posteriori distribution p(x,θ|m) representing the three-dimensional information of the object (4) and the imaging geometry including the motion of the object.

20. A medical x-ray device (5) arrangement according to claim 19, characterized in that the three-dimensional information of the object (4) is one or more two-dimensional images representing X-ray attenuation coefficient along slices through the object.

21. A medical x-ray device (5) arrangement according to claim 19, characterized in that the three-dimensional information of the object (4) is a three-dimensional voxel representation of the X-ray attenuation in the object.

22. A medical X-ray device (5) arrangement according to claim 19, characterized in that the medical X-ray device arrangement comprises means (15) for modelling the measurement as $$m = A_\theta x + e,$$

where matrix $A_\theta$ contains the weights describing how much each voxel contributes to the X-ray attenuation along the X-ray paths and the noise e is independent of object image vector x and the geometry parameter vector θ leading to the likelihood distribution $$p(m|x,\theta) = p_{noise}(m - A_\theta x).$$

23. A medical X-ray device (5) arrangement according to claim 19 characterized in that the medical X-ray device arrangement comprises means (15) for modelling the object (4) mathematically so that X-radiation attenuates when passing the object (4), which means that every image voxel is nonnegative.

24. A medical X-ray device (5) arrangement according to claim 19, characterized in that the medical X-ray device arrangement comprises means (15) for modelling the object (4) mathematically by the formula:

$$p_{pr}(x) = \exp\left(-\alpha \sum_N U_N(x)\right)$$

where the sum is taken over a collection of 3D neighbourhoods N and the value $U_N(x)$ depends only on the values of voxels belonging to the neighborhood N, and α is a positive regularization parameter used to tune the width of the prior distribution.

25. A medical x-ray device (5) arrangement according to claim 19, characterized in that the 3D tomographic problem is divided into a stack of 2D tomographic problems and on every such 2D problem, the medical X-ray device arrangement comprises means (15) for modelling the object (4) mathematically by the formula:

$$p_{pr}(x) = \exp\left(-\alpha \sum_N U_N(x)\right)$$

where the sum is taken over a collection of 2D neighbourhoods N and the value $U_N(x)$ depends only on the values of pixels belonging to the neighborhood N, and α is a positive regularization parameter used to tune the width of the prior distribution, and the 2D tomographic problems are related to each other by the formula $$pr3D(x(j)) = \exp(-\gamma \Sigma\Sigma |x(j)[k,q] - x(j-1)[k,q]|),$$

where the sums are taken over all pixels (k=1, ..., K, q=1, ..., Q) and γ>0 is another regularization parameter.

26. A medical X-ray device (5) arrangement according to claim 25, characterized in that the neighborhood systems comprise two neighboring pixels xj, xk or voxels xj, xk and $U_N(x)$ calculates a power of the $$p_{pr}(x^{(j)}) = \exp\left(-\alpha\left(\sum_{k=1}^{K-1}\sum_{q=1}^{Q} |x^{(j)}[k,q] - x^{(j)}[k+1,q]|^s + + \sum_{k=1}^{K}\sum_{q=1}^{Q-1} |x^{(j)}[k,q] - x^{(j)}[k,q+1]|^s\right)\right)$$

absolute value of the difference, leading to the formula where s is a positive real number and α is a regularization parameter used to tune the width of the prior distribution.

27. A medical X-ray device (5) arrangement according to claim 26, characterized in that the medical X-ray device arrangement comprises means (15) for modelling the object (4) mathematically by setting s=1 corresponding to total variation (TV) prior describing objects consisting of different regions with well-defined boundaries.

28. A medical X-ray device (5) arrangement according to claim 19, characterized in that the medical X-ray device arrangement comprises means (15) for modelling the object (4) mathematically by assuming that mathematical modelling is qualitative structural information of the target where the structural information is encoded in prior distributions that are concentrated around image vectors x that correspond to the physiological structures of the target.

29. A medical X-ray device (5) arrangement according to claim 19, characterized in that the medical X-ray device arrangement comprises means (15) for modelling the object (4) mathematically by assuming that mathematical modelling comprises a list of possible attenuation coefficient values in the object.

30. A medical X-ray device (5) arrangement according to claim 19, characterized in that the medical X-ray device arrangement comprises means (15) for modelling the object (4) mathematically by assuming that the X-ray imaging geometry, such as X-ray source position, has unknown error modelled in the distribution p(m|x,θ).

31. A medical X-ray device (5) arrangement according to claim 19, characterized in that the medical X-ray device arrangement comprises means (15) for modelling the object (4) mathematically by assuming that X-radiation measurement noise is Poisson distributed.

32. A medical X-ray device (5) arrangement according to claim 19, characterized in that the medical X-ray imaging is dental radiography.

33. A medical X-ray device (5) arrangement according to claim 19, characterized in that the medical X-ray imaging is surgical C-arm imaging.

34. A medical X-ray device (5) arrangement according to claim 19, characterized in that the medical X-ray imaging is mammography.

35. A medical X-ray device (5) arrangement according to claim 19, characterized in that the medical X-ray device arrangement comprises means (15) for producing three-dimensional information of the object (4) on the basis of the maximum a posteriori estimator (MAP), which is calculated by the equation:

$$p(y_{MAP}|m) = \max p(y|m)$$

m representing projection data and $y=(x,\theta)$ representing the vector composed of the object image vector and the geometry parameter vector, and where the maximum on the right hand side of the equation is taken over all y.

36. A medical X-ray device (5) arrangement according to claim 19, characterized in that the medical X-ray device arrangement comprises means (15) for producing three-dimensional information of the object (4) on the basis of the conditional mean estimator (CM), which is calculated by the equation $$y_{CM} = \int y p(y|m) dy$$

where m represents projection data and $y=(x,\theta)$ represents the vector composed of the object image vector and the geometry parameter vector.

* * * * *